United States Patent [19]
Manoil et al.

[11] Patent Number: 4,914,025
[45] Date of Patent: Apr. 3, 1990

[54] EXPORT OF INTRA-CELLULAR SUBSTANCES

[76] Inventors: Colin Manoil, 359 Heath St., Chestnut Hill, Mass. 02167; Jonathan Beckwith, 84 Appleton Rd., Cambridge, Mass. 02138; Michael Syvanen, 31 Winthrop Rd., Brookline, Mass. 02146; Ralph R. Isberg, 1080 Noel Dr. #5, Menlo Park, Calif. 94025; Charles S. Hoffman, 55 Arbor St., Wenham, Mass. 01984; Andrew Wright, 16 Regent St., West Newton, Mass. 02165

[21] Appl. No.: 805,486

[22] Filed: Dec. 5, 1985

[51] Int. Cl.$^4$ .................. C12P 21/00; C12P 21/02; C12N 12/00
[52] U.S. Cl. .................. 435/69.8; 435/172.3; 435/320; 435/91; 435/21; 435/34; 435/6; 435/818; 435/849; 435/196; 536/27; 935/47; 935/48; 935/72
[58] Field of Search .............. 435/172.3, 91, 6, 317, 435/320, 848, 859; 935/47, 48, 72; 536/27

[56] References Cited

PUBLICATIONS

Casadaban, M. J. et al., β-Galactosidase Gene Fusions for Analyzing Gene Expression in *E. coli* and Yeast; Methods in Enzymology (1983), vol. 100, pp. 293-308.
Stachel, S. E. et al.; A Tn3 lacZ Transposon for the Random Generation of β-galactosidase Gene Fusions: Application to the Analysis of Gene Expression in Agrobacterium; EMBO Journal, 4 (4), pp. 891-898 (1985).
Berg, D. E. and C. M. Berg; The Prokaryotic Transposable Element Tn5; Biotechnology 1: 417-435 (1983).
Manoil, C. and J. Beckwith; TNphoA: A Transposon Probe for Protein Export Signals; Proc. Nat'l. Acad. Sci., 82, pp. 8129-8133 (1985).
Guo L-H. and R. Wu; Exonuclease III: Use for DNA Sequence Analysis and in Specific Deletions of Nucleotides; Methods in Enzymology, 100 (1983), pp. 60-95.
Hoffman, C. S. and A. Wright; Fusions of Secreted Protiens to Alkaline Phosphatase: An Approach for Studying Protein Secretion; Proc. Nat'l. Acad. Sci., 82 (1985), pp. 5107-5111.
Kroos, L. and D. Kaiser; Construction of Tn5 lac, a Transposon That Fuses lacz Expression to Exogenous Promoters, and Its Introduction into *M. xanthus*; Proc. Nat'l. Acad. Sci., 81 (1984), pp. 5816-5820.
Michaels and Beckwith, Annu. Rev. Microbiol., vol. 36, pp. 435-465.
Beckwith and Silhavy, Meth. Enzy., vol. 97, pp. 3-11 (1982).
Isberg et al., J. Mol. Biol., vol. 150, pp. 15-32 (1981).

*Primary Examiner*—Robin Teskin

[57] ABSTRACT

An export sequence of export DNA can be identified by transforming a population of cells with a vector having a transposon that includes a structural gene encoding a detectable compound, positioned between insertion sequences. The structural gene encodes a detectable compound that, in wild-type organisms, is translated with an export peptide effective to export the compound. Since the transposon lacks DNA coding for an export sequence capable of exporting the detectable gene product, transformants that export the gene product include a DNA fusion of the transposon to export DNA from the parent cell, in a position to allow expression of the fused DNA. The transformants are analyzed to locate the export DNA or a gene comprising it, and the position of the export DNA in the cell's genome is determined; the orientation of the insertion also is determined. Having identified cell genes that naturally contain export DNA, the export DNA is cloned and fused to a gene encoding a product whose production and export are desired. For example, a cell is engineered to produce and export a desired product, to enable easier substance recovery and to improve cell tolerance for high levels of the desired product.

15 Claims, 2 Drawing Sheets

EXPORT OF INTRA-CELLULAR SUBSTANCES

BACKGROUND OF THE INVENTION

This invention was made with Government support in the form of grants from the NIH and received support also under a grant from the Arthritis Foundation and under grant MV-5M from the American Cancer Society, the U.S. Government has certain rights in the invention.

This invention relates to export of substances from a cell.

Often proteins or other substances produced within the cellular cytoplasm include an amino acid sequence, called a "signal" or "export" sequence, that effects export of the substance from the cytoplasm into, e.g. fluid medium surrounding the cell or into the cell's periplasmic space. More specifically, the export signal of a protein is that part which permits the protein to pass through the inner cytoplasmic membrane to either the outer part of the membrane, the periplasmic space, or the surrounding medium. In the latter two cases such signals often are termed secretory signals, and the protein is said to be secreted. In this patent application, the term "export sequence" includes all amino acid sequences that effect transport out of the cytoplasm, regardless of the final destination (outer membrane, external medium, periplasm, etc.) of the substance being exported from the cytoplasm. The term "export DNA" refers to DNA encoding an export sequence.

Fusion proteins have been used to study export as described below.

Michaels and Beckwith (1982) Annu. Rev. Microbiol. 36: 435–465 and Beckwith and Silhavy (1982) Meth. Enzy. 97: 3–11 disclose in vitro fusions of varous DNA sequences to beta-galactosidase to determine whether those sequences are able to effect export of beta-galactosidase.

Genes encoding detectable products have been used to study promoters. For example, the beta-galactosidase gene has been inserted in vivo using a transposon adjacent to promoters to determine the promoter's ability to regulate expression of that gene.

SUMMARY OF THE INVENTION

In general, the invention features identifying an export sequence or export DNA of a cell by transforming a population of cells with a vector having a transposon that includes a structural gene encoding an extracellular detectable compound. By "transposon" is meant a genetic element comprising a pair of inverted repeat sequences, called insertion sequences, one member of which is at either end of the transposon; between the repeats are genes responsible for transposition and regulation of transposition; the gene encoding the detectable compound is positioned between those insertion sequences. By "extracellular detectable compound" is meant a peptide or other gene product that in wild-type organisms is exported, and which has, or can be processed by the cell to have, an activity that can be readily detected, e.g., the ability to bind selectively to a labelled compound or the ability to participate in an enzymatic reaction. Enzymes, enzyme substrates, and immunological binding partners are the preferred detectable compounds. The transposon lacks DNA encoding an export peptide effective to export the compound, e.g., because the export DNA of the wild-type gene has been deleted or disenabled. Therefore, the transformants that are able to secrete the compound are cells that have undergone an in vivo fusion of the transposon DNA to export DNA from the parent cell, in a position allowing expression of the fused DNA.

Preferably, the transposon is Tn5, and the detectable gene product is alkaline phosphatase, e.g., the E. coli phoA gene product. Also, cells that are transformed with the vector are unable to produce the detectable product at all (e.g. because they lack DNA coding for it or they lack regulatory DNA necessary to express it). Also preferably, the structural gene coding for the product preferably is not expressed in transformants that have not undergone the transposition, e.g., because the vector lacks regulatory DNA positioned to express the gene. Also preferably, the transposon has no nonsense codons in frame with and upstream from the gene—i.e., in the transposon junction sequence through which transcription occurs. In this way, the gene can be expressed in cells that have not been modified to permit them to read through non-sense codons. Most preferably at least one transposon insertion sequence has the codon TGG in frame with, and upstream from, the gene. More specifically, the codon is included in the sequence given in FIG. 2. Most preferably, the transposon insertion sequence includes the sequence XCT-GAC-TCT-TAT-ACA-CAA-GTA.

Having isolated a cell that exports the detectable product, its genome can be analyzed to locate the export DNA, or a gene comprising it, and the position of the export DNA in the cell's genome can be determined; the orientation of the insertion can also be determined. Having identified cell genes that naturally contain export DNA, the export DNA can be cloned and fused to a gene encoding a product whose production and export are desired. For example, when engineering a cell to produce a desired substance, it is useful to induce export of the substance from the cell to enable easier substance recovery and to reduce intracellular levels of the desired substance which may be detrimental to the cell or may be degraded by the cell.

Accordingly, the invention features expression vectors for producing a desired product, in which a heterologous structural gene coding for the product is fused to export DNA located by the above method; by heterologous is meant a structural gene that, in wild-type organisms, is not expressed as a fusion with the export signal. And the invention features cells transformed with such vectors, as well as methods of producing the product by culturing the transformed cells and recovering product from the extracellular medium.

Other features and advantages of the invention are apparent from the following description of the preferred embodiment and from the claims.

DESCRIPTION OF THE PREFERRED EMBODIMENTS

The figures will first briefly be described.

I. Drawings

Figure 1:
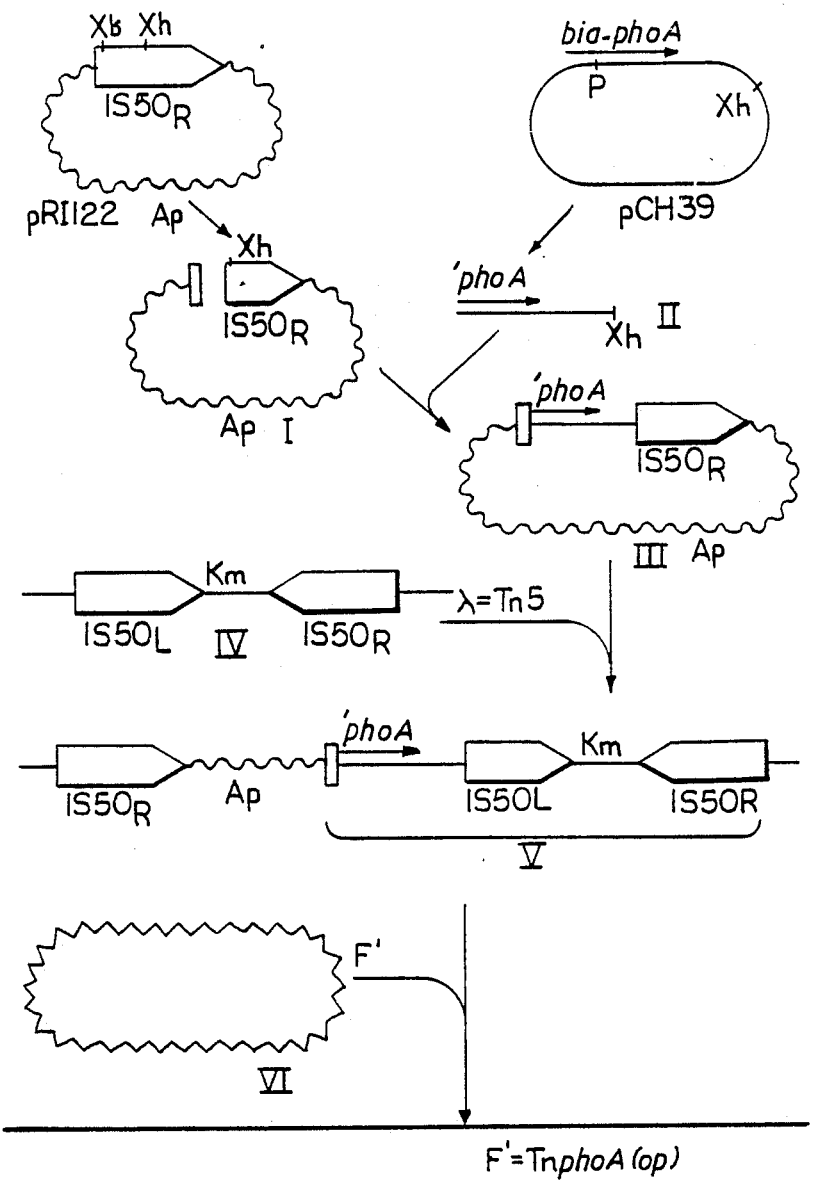
FIG. 1 is a diagramatic representation of the construction of the DNA sequence of Tn phoA.

II. Structure and Construction of the Transposing Vector

The transforming vector has a transposon that includes a gene encoding an easily detectable product; the gene is one that naturally is expressed with an export sequence, but, in the transposon, the export DNA has been removed or otherwise disabled. The detectable product should be one whose activity and ability to be exported is retained when fused to other peptide fragments.

Generally, the detectable product gene (which we will call gene A) is inserted into an insertion sequence as near as possible to the transposon end to which fusion is desired, without destroying the insertion function. This process is performed using conventional recombinant DNA technology, and any manipulation of the transposon, e.g. Tn5, also is performed by standard techniques, for example those generally described by Bruijn and Lupski 1984 (Gene 27: 131). Other suitable transposons are Tn 917, bacteriophage mu, or others described in *DNA Insertion Elements, Plasmids and Episomes* Bukliari, Shapiro and Adhya, Cold Spring Harbor Press, Cold Spring Harbor, NY, 1977; or Berg et al. *Microbiolgy* 1981, Shlessinger (Ed.) Am. Soc. Microbiol. Press, Washington, DC 1981.

As detailed below, when this transposon transposes in vivo into bacterial DNA, it may place gene A near to an export sequence of a gene from the host bacterium, (which we will call gene B) and that when the host gene B is expressed, then the export signal sequence, a part of gene B, and gene A will be transcribed as one unit, along with a few intervening bases from the insertion sequence. If the insertion is also such that the export signal sequence and gene A are in the same reading frame, then translation will give a hybrid protein consisting of an exort signal sequence, a part of gene B, and gene A. This protein will be secreted from the cell and the activity of gene A can be detected.

While the vector is exemplified below by a plasmid, phage which contain a copy of Tn5 or another equivalent transposon also can be used in this invention. Preferred is phage lambda 431 [b221 cI857 rex::Tn5, Isberg et al. (1982) Cell 30: 883-892]. Finally, plasmids, or other vectors, containing a gene encoding an easily detectable product, are suitable for use to place the gene into a transposon.

A preferred carrier for the transposon gene encoding the easily detectable product is plasmid pCH39 which is a derivative of pBR322 carrying bla-phoA fusion with a PstI site at the junction between these sequences (Hoffman and Wright, (1985) Proc. Nat'l. Acad. Sci. 82: 5107). Similarly any vector, containing an insertion sequence with a restriction site near to the end at which it is desirable to place the above gene, can be used. Preferred is plasmid pRI122 which is a derivative of pBR322 carrying an insert of IS50$_R$ with an XbaI site near its left end (Isberg and Syvanen (1981) J. Mol. Biol. 150: 15-32).

Examples of such vectors are given below:

(a) Construction of Tn phoA (op)

Steps used to construct Tn phoA (op) are diagrammed in FIG. 1 and outlined below. This construction results in the placement of a DNA fragment encoding most of the mature (structural) portions of alkaline phosphatase (lacking the coding region for the export signal peptide and five additional amino terminal residues) close to the left end of Tn5. When Tn phoA (op) is transposed into a gene such that the phoA gene is in both the appropriate orientation and translational reading frame, compared to those of the target gene, a hybrid protein containing amino terminal residues of the target gene product fused to the alkaline phosphatase polypeptide results. This target gene may be present either on the chromosome of a microorganism, or within a plasmid or phage. The location of insertion of the transposon is readily analyzed by standard genetical techniques and by restriction enzyme analysis, for example, using the general techniques disclosed by Maniatis et al., *Molecular Cloning*, Cold Spring Harbor Laboratory 1982.

Referring to FIG. 1 pRI122 is a derivative of pBR322 carrying an insert of IS50$_R$ which is modified by the presence of an XbaI site near its left end (Isberg et al. 1982 Cell 30: 883). Within the IS50 sequence are a unique XbaI and XhoI site shown as Xb and Xh in the figure. The plasmid sequences are shown as a wavy line and comprise a gene encoding resistance to ampicillin (Ap). The IS50 sequence is shown as an empty arrow. Species I is derived from pRI122 by sequential treatment with XbaI, Ba131 exonuclease and XhoI.

pCH39 is also a derivative of pBR322 carrying bla-phoA sequences (Hoffman and Wright, id.). This plasmid comprises PstI (shown as a P) and XhoI sites, a PstI site being at the junction between the bla and the phoA sequences. pCH39 is treated with PstI, T4 DNA polymerase and XhoI to give a DNA fragment with a XhoI and a blunt end, shown as species II in FIG. 1.

Species I and II are purified by agarose gel electrophoresis and subsequently mixed together in the presence of T4 ligase to create species III. This DNA is transformed into *E. coli* selecting for cells resistant to ampicillin. Phage λ 431 (Isberg and Syvanen, 1981, Journal of Molecular Biology 150: 15) is phage lambda into which Tn5 has been inserted, shown as species IV in FIG. 1. Tn5 consists of a left and right hand IS50 sequence, referred to as IS50$_L$ and IS50$_R$ respectively, and an intervening gene encoding kanamycin (Km) resistance. The resulting species V is a recombination product of species III and IV and contains Tn5 linked to phoA, inserted into the lambda phage DNA. Tn phoA is recovered from species V after transposition into the F factor, F42 ts114 lac, by conjugation with recipient cells. Selection is for kanamycin resistance and a Lac+ phenotype. Those cells which are also ampicillin sensitive are selected and one such strain, termed F42 ts114 lac zzf-1::Tn phoA (op), is shown as species VII in FIG. 1. This strain comprises an F factor containing Tn phoA (op) which can be readily moved into other bacterial strains, and from which the Tn phoA (op) sequences can transpose into other DNA sequences.

(b) Construction of Tn phoA

Figure 2:
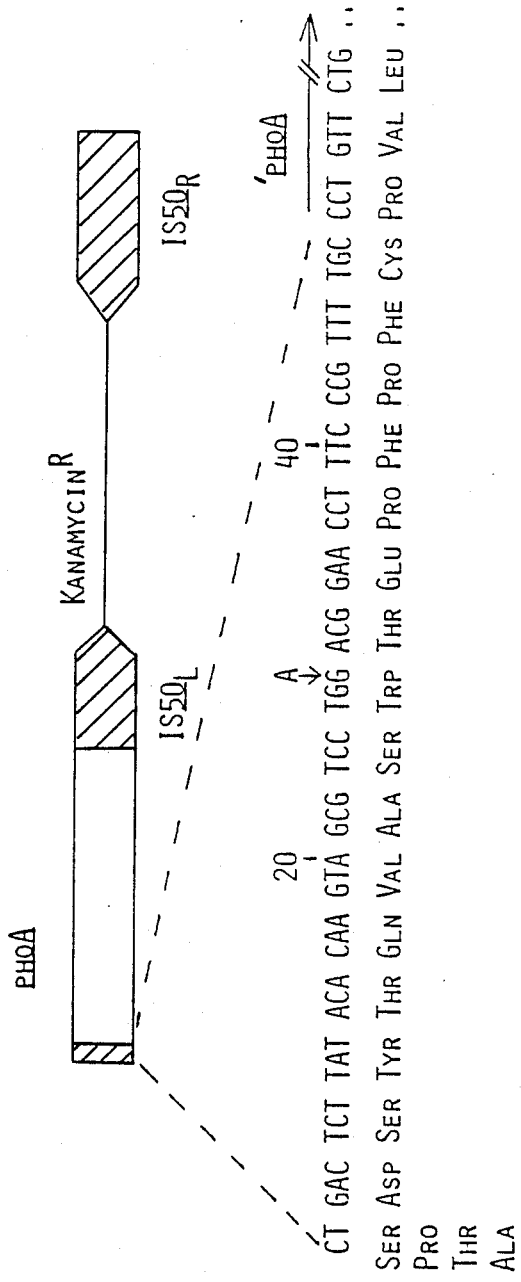
FIG. 2 is a diagramatic representation of the DNA sequence of Tn phoA.

The use of Tn phoA (op) is limited to strains which have a nonsense suppressor function, such as the strain CC125. This supressor is required since the part of IS50$_L$ DNA upstream from the phoA sequences has nonsense codons within each translational reading frame, thus preventing translation of the alkaline phosphatase gene unless a supressor mutation is present. The sequence of bases on the left hand side of IS50$_L$ is shown in FIG. 2, it comprises only 50 base pairs. In order to remove the requirement for a supressor mutation, a fusion plasmid (b-101), derived from insertion of the phoA IS50 sequence, from Tn phoA (op), into pBR322 which resulted in secretion of alkaline phosphatase, was grown in a mutator strain (CC130), with selection for cells acquiring plasmid-linked, suppressor independent, increased expression of alkaline phosphatase activity. One such strain (B-4) was derived which contained a mutant plasmid, the Tn phoA region of which was then transferred back into pBR322 to give the derivative Tn phoA. The nucleotide sequence of this derivative was derived by standard methodology and is presented in FIG. 2. The base change from an A to a G residue changed a nonsense codon to a sense codon and thus removed the dependence on supressor mutations.

Referring to FIG. 2 the IS50$_{L\&R}$ sequences are shown as filled in parts of arrows and the phoA sequence as an unshaded part of the arrow. The position of the kanamycin gene encoding resistance to kanamycin is shown as is the nucleotide sequence, and corresponding amino acid sequence, of the left hand end of the IS50$_L$ region. The base pairs are numbered from the left hand end and the position of substitution (at base 29) of an A for a G, is shown. Such a substitution gives rise to Tn phoA, while the native sequence is termed Tn phoA (op).

III. Transformation of Bacterial Cells

Bacterial cells which can be transformed with DNA containing Tn5, or another transposon, are suitable. Particularly suitable are: *E. coli* CC118 (araD139 Δ ara, leu) 7697 ΔlacX74 ΔphoA20 galE galK thi rpsE rpoB argE$_{AM}$ and recA1), CC126 (CC118 araC leu$_{op}$ sup9 lamB), CC125 (CC126 sup6), CC149 (MC1000 phoR/F42 lacI3) and CC130 (MPh 44 mutD5).

Transpositions can be selected into a chromosome or into a vector DNA using standard methodology. For example to select transpositions of Tn phoA (op) or Tn phoA into plasmids pBR322 or pBR325, an Flac factor carrying the transposon to be inserted (F42ts114 lac zzf-1::TnphoA (op) or F42 lacI3 zzf-2::TnphoA) is introduced into a phoA strain (CC125 or CC118) carrying monomeric pBR322 or pBr325. To enrich for transpositions into the plasmid from the Flac, single colonies are resuspended in LB and dilutions plated onto LB agar containing tetracycline (20 μg/ml) or ampicillin (200 μg/ml), kanamycin (300 μg/ml) and XP (5-bromo-4-chloro-3-indolyl phosphate, 40 μg/ml). The high concentration of kanamycin in this medium enriches for cells carrying insertions of the transposon into the multicopy plasmid. After two days incubation at 37° C., blue colonies are usually struck out on the same medium, and plasmid DNA is prepared from these cells after an additional day of growth at 37° C. Alternatively, plasmid DNA is sometimes made from the mixture of colonies which are grown on the high kanamycin concentration agar without additional purification. Plasmid DNA is used to transform phoA recipient cells, with selection for transformants growing on TYE agar containing kanamycin (30 μg/ml) and XP (40 μg/ml). Insertions leading to hybrid proteins with alkaline phosphatase activity give blue colonies on this medium, whereas other insertions give white colonies. Specifically, alkaline phosphatase activity of strains is determined using the standard para-nitrophenyl phosphate assay of Michaelis et al. (1983) J. Bacteriol. 154: 366.

The fusion of phoA with a target gene results in the production of a hybrid protein containing a part of the target gene and the alkaline phosphatase gene. Such hybrids are efficiently precipitated by antibody to the alkaline phosphatase or to the target gene, depending on the amount of target gene protein present, and/or on the three-dimensional structure of the hybrid protein. These hybrid proteins are stable and enzymically active.

The method described above also results in expression of alkaline phosphatase when the transposon is fused to a transmembrane protein. Expression is only observed if the insertion is such that it places the alkaline phosphatase moiety in the periplasmic space of the bacterium.

IV. Locating and EValuating Export DNA Sequences

Tn phoA (op) and Tn phoA can be used for the study of exported proteins which cannot be readily detected. The fusion of alkaline phosphatase to the export signal sequence and thence the promotor of these proteins allows the ready determination of both promotor and secretory control mechanisms by assaying for alkaline phosphatase activity. In addition, using conventional techniques described below, the enzymatically active hybrid protein generated by such fusions can be analyzed to determine the position of regions of the gene, into which the insertion was made, encoding the external part of a transmembrane protein. Similarly the orientation of these genes may be determined by analysis of the DNA created by such an insertion, using restriction enzyme technology. A further use is the identification of unknown, or unidentified, proteins which contain signal sequences by randomly inserting these fusion transposons into the DNA of interest, selecting for microoganisms able to secrete the alkaline phosphatase, and characterizing genetically and physiologically the strains resulting.

Conventional techniques can be used to clone the gene or export signal sequence into which the transposon has been inserted. Such methodology involves either the construction of a gene library from the DNA comprising the inserted transposon, and subsequently identifying those clones with transposon sequences; or designing the transposon such that it can function as a vector, using the technique generally described for Gram positive bacteria such as *Bacillus subtitis* with transposon Tn917 (Youngman et al. 1984, Mol. Gen. Genetics 195: 424). In essence the transposon has a plasmid origin of replication, a gene encoding a selectable trait, and unique restriction enzyme sites. When DNA into which this transposon has been inserted is isolated, cut at a unique restriction enzyme site, and self-ligated, it will form a plasmid which can transform a bacterial cell and contains a part of the gene into which the transposon was inserted. Standard methodology can then be used to analyze and sequence this DNA; see generally Maniatis et al., *Molecular Cloning*, Cold Spring Harbor Laboratory, Cold Spring Harbor, NY, 1982.

The export DNA isolated by the above methods can be used to produce vectors which can express and export a desired product. The gene encoding the desired product can be ligated to the cloned export DNA directly or to the alkaline phosphatase gene, upstream from the export DNA. The vector is used to transform a host cell, which produces the desired product, either fused to the export sequence or as a hybrid protein with alkaline phosphatase. This product can be recovered by conventional methods.

V. Deposit

A strain containing the F' factor comprising Tn phoA has been deposited with the American Type Culture Collection, Rockville, MD and assigned the number 53322.

OTHER EMBODIMENTS

Other embodiments are within the following claims.

This methodology is not limited to Tn5 in *Escherichia coli* but to any transposon that functions in any particular microorganism. For example in Gram positive bacterial, Tn917 (Youngman et al. 1983 Proc. Nat. Acad. Sci. 80: 2305) and an extracellular protease gene of

*Bacillus subtitis* would be a suitable combination. Transposon Tn5 is of use in analyzing a variety of microorganisms, since it has a wide host range. For example *Caulobacter crescentus* (Bellofatto et al., (1984) Proc. Nat'l. Acad. Sci. 81: 1035).

Alkaline phosphatase genes from any source of mircoorganisms can be utilized so long as that gene can be transcribed and translated within the host system; as can any other gene encoding an easily detectable product that is naturally translated with a signal sequence.

The above method can also be used to select efficient exporters from various organisms that have been engineered to produce proteins using foreign signals. Specifically organisms are transformed with DNA that includes various foreign export signals fused to the structural gene of interest. Then cells that are efficient exporters are selected using the above described vector. Finally, original genes of the selected organisms are reconstructed by eliminating phoA sequences using standard in vitro methods.

It is also possible to use the above method to select variants of a cell type that are able to export a protein that is normally cytoplasmic.

We claim:

1. A method for identifying a transformed bacterial cell comprising an export DNA sequence, said method comprising:
   providing a vector comprising a transposon, said transposon comprising a pair of repeated insertional sequences that are inverted with respect to one another, said vector further comprising a structural gene whose N-terminal-encoding end is adjacent the end of one of said insertional sequences, said structural gene encoding alkaline phosphatase, said transposon lacking DNA encoding an export peptide positioned to export alkaline phosphatase produced by expression of said gene, said cell lacking the ability to secrete alkaline phosphatase prior to said transposition;
   transforming said cell with said vector and growing transformants to allow transposition to occur;
   screening for transformants able to secrete alkaline phosphatase in which an export DNA sequence of said bacterial cell has been positioned adjacent the N-terminal encoding end of said gene encoding alkaline phosphatase.

2. The method of claim 1 wherein, prior to said transportation, said cell does not express said structural gene.

3. The method of claim 2 wherein said vector lacks regulatory DNA positioned to effect expression of said structural gene.

4. The method of claim 1 wherein said method further comprises analyzing the genome of said alkaline phosphatase secreting transformants to locat said export DNA or the gene comprising said export DNA.

5. The method of claim 1 wherein said transposon is Tn5.

6. The method of claim 1 wherein said gene is *E. coli* phoA.

7. The method of claim 1 wherein said transposon contains at least one non-sense codon in frame with, and upstream from the N-terminal end of said gene, said cell having a non-sense suppressor function to translate and transcribe through said non-sense codon.

8. The method of claim 1 wherein said transposon has no non-sense codons in frame with, and upstream from, said gene, wherein said cell has no non-sense suppressor function and is able to translate and transcribe said transposon at least through said entire gene.

9. A transposon comprising a structural gene positioned between a pair of repeated insertional sequences that are inverted with respect to one another, said structural gene encoding alkaline phosphatase, said transposon lacking DNA encoding an export peptide positioned to export alkaline phosphatase produced by expression of said gene, said transposon being capable of insertion of said structural gene into the genome of a host bacterial cell.

10. The transposon of claim 9 wherein said insertional sequences are IS50 sequences.

11. The transposon of claim 9 wherein said structural gene is the *E. coli* phoA structural gene.

12. The transposon of claim 9 wherein said transposon has no non-sense codons in frame with, and upstream from the N-terminal encoding end of, said gene.

13. The transpopson of claim 12 wherein at least said transposon insertion sequence comprises the sequence TGG.

14. The transposon of claim 13 wherein said transposon insertion sequence comprises the sequence:
XCT-GAC-TCT-TAT-ACA-CAA-GTA.

15. The Tn5/pho A transposon contained in cell deposit ATCC 53322.

* * * * *